United States Patent
Bradley et al.

(10) Patent No.: US 7,349,738 B1
(45) Date of Patent: Mar. 25, 2008

(54) DETECTING ATRIAL EVOKED RESPONSE

(75) Inventors: Kerry Bradley, Glendale, CA (US); Laurence S. Sloman, West Hollywood, CA (US)

(73) Assignee: Pacesetter, Inc., Sylmar, CA (US)

( * ) Notice: Subject to any disclaimer, the term of this patent is extended or adjusted under 35 U.S.C. 154(b) by 513 days.

(21) Appl. No.: 10/370,815

(22) Filed: Feb. 19, 2003

(51) Int. Cl.
A61N 1/08 (2006.01)

(52) U.S. Cl. ........................................... 607/28

(58) Field of Classification Search ................ 607/9, 607/17, 27, 28
See application file for complete search history.

(56) References Cited

U.S. PATENT DOCUMENTS

| | | | |
|---|---|---|---|
| 4,549,548 A | 10/1985 | Wittkampf et al. | 128/419 PG |
| 4,712,555 A | 12/1987 | Thornander et al. | 128/419 PG |
| 4,788,980 A | 12/1988 | Mann et al. | 128/419 PG |
| 4,858,610 A | 8/1989 | Callaghan et al. | 128/419 PG |
| 4,940,052 A | 7/1990 | Mann et al. | 128/419 PG |
| 4,944,298 A | 7/1990 | Sholder | 128/419 PG |
| 4,991,583 A | 2/1991 | Silvian | 128/419 PG |
| 5,431,693 A * | 7/1995 | Schroeppel | 607/28 |
| 5,443,485 A * | 8/1995 | Housworth et al. | 607/28 |
| 5,466,254 A | 11/1995 | Helland | 607/123 |
| 5,476,483 A | 12/1995 | Bornzin et al. | 607/17 |
| 5,713,934 A | 2/1998 | Leckrone | 607/28 |
| 5,873,898 A | 2/1999 | Hemming et al. | 607/28 |
| 5,941,903 A * | 8/1999 | Zhu et al. | 607/13 |
| 6,144,881 A * | 11/2000 | Hemming et al. | 607/28 |
| 6,163,724 A * | 12/2000 | Hemming et al. | 607/28 |
| 6,473,649 B1 * | 10/2002 | Gryzwa et al. | 607/28 |
| 6,477,417 B1 | 11/2002 | Levine | 607/9 |
| 6,711,439 B1 * | 3/2004 | Bradley et al. | 607/9 |
| 2002/0116031 A1 * | 8/2002 | Vonk | 607/28 |
| 2002/0193834 A1 | 12/2002 | Levine | 607/9 |

\* cited by examiner

*Primary Examiner*—Mark Bockelman
*Assistant Examiner*—Eric D. Bertram

(57) ABSTRACT

A pulse is delivered to the atrium using an electrode configuration that includes at least a pulse cathode electrode. Cardiac activity in the atrium is sensed using a unipolar electrode configuration to provide a sensed signal wherein the unipolar electrode configuration does not include the pulse cathode electrode. A determination as to whether the pulse caused an atrial evoked response is made based on a maximum derivative value of the sensed signal with respect to time, a comparison of the sensed signal to a parameter or an integral of the sensed signal with respect to time.

6 Claims, 17 Drawing Sheets

DETECTING ATRIAL EVOKED RESPONSE

TECHNICAL FIELD

The subject matter disclosed herein generally relates to methods and systems for providing cardiac pacing therapy. More particularly, the subject matter concerns methods and implantable devices for sensing atrial evoked responses.

BACKGROUND

Implantable pacing devices often include electrodes to deliver pulses and/or to sense cardiac activity in response to delivered pulses. Cardiac activity related to a delivered pulse is typically known as an "evoked response" (e.g., an electrical signal arising from atrial or ventricular cardiac tissue depolarization in response to delivery of a pacing pulse). However, many issues complicate sensing and/or detection of evoked responses. For example, post-pulse electrode polarization can interfere with detection of an evoked response and/or produce a "polarization artifact" in a detected signal. Post-pulse electrode polarization results primarily from capacitive charging of an electrode-electrolyte interface during delivery of a pacing pulse. Upon termination of the pacing pulse, the post-pulse electrode polarization decays over time, generally in an exponential fashion like a capacitor. Characteristics of post-pulse electrode polarization generally depend on a variety of parameters, such as, electrode materials, electrode geometry, tissue characteristics, tissue contact, stimulation energy, and others, many of which vary over time. Consequently, an elaborate characterization of post-pulse electrode polarization is impractical, especially when one considers resource limitations inherent in implantable pacing devices.

U.S. Pat. No. 6,163,724, entitled "Microprocessor capture detection circuit and method", to Hemming, et al. ('724 patent), addresses post-pulse electrode polarization through use of filtering. More specifically, the '724 patent discloses "an adaptive nonlinear filtering technique referred to as 'Negative Peak Tracking' (or 'NPT') that removes the initial residual [post-pulse] polarization signal, and then passes only that portion of the sensed signal where a change in the sign of the slope occurs" (col. 7, lines 4-8). According to the '724 patent, such filtering, in combination with "[j]udicious selection of comparator threshold levels by a user[,] improves the reliability of event discrimination [capture versus non-capture events]" (col. 7, lines 26-28).

Another issue in detection of evoked responses stems from differences in ventricular and atrial pacing. Thus, approaches to detection of evoked responses in ventricular pacing may not apply directly to detection of evoked responses in atrial pacing. For example, U.S. Pat. No. 5,713,934, entitled "Evoked and spontaneous cardiac activity detection in a dual-chamber electronic pacemaker and method", to Leckrone, ('934 patent) discloses a pacing system that uses ventricular pacing electrodes and atrial pacing electrodes for sensing. According to the '934 patent, a ventricular evoked response typically peaks at about 30 milliseconds following a ventricular pulse and ranges in amplitude from about 3 millivolts to about 20 millivolts; whereas, an atrial evoked response typically occurs within 20 milliseconds of an atrial pulse with an amplitude generally smaller than that of a ventricular evoked response.

While other pacing and sensing electrode configurations are possible, none of the patents referred to herein discuss the relationship between post-pulse timing of an atrial evoked response and electrode configuration. For example, U.S. Pat. No. 4,549,548, entitled "Pacemaker system with automatic event-programmed switching between unipolar and bipolar operation", to Wittkampf, et al., issued Oct. 29, 1985 ('548 patent), discloses a pacemaker system capable of both unipolar and bipolar sensing wherein "considerations for unipolar and bipolar sensing vary at different times in the pacing cycle, dependent upon the next anticipated event" (col. 2, ll. 12-19). Thus, the '548 patent focuses on the relationship between electrode configuration and "the next anticipated event" and not other considerations such as, but not limited to, electrode polarization. Likewise, U.S. Pat. No. 4,858,610, entitled "Detection of Cardiac Evoked Potentials", to Callaghan, et al., issued Aug. 22, 1989 ('610 patent), fails to discuss the relationship between post-pulse timing of an atrial evoked response and electrode configuration.

U.S. Pat. No. 5,873,898, entitled "Capture Detection Circuit for Pulses and Physiological Signals", to Hemming, et al., issued Feb. 23, 1999 ('898 patent), discloses a system for pacing and sensing and presents data from a canine ventricular pacing study for pacing and sensing in both unipolar and bipolar electrode configurations. More specifically, in Table 3 of the '898 patent, "Event 15" uses a ring-to-can electrode configuration for ventricular sensing (col. 25, ll. 56-57). While the '898 patent alludes to enhanced accuracy for tip-to-can (unipolar) ventricular sensing when compared to tip-to-ring (bipolar) ventricular sensing (col. 29, ll. 51-55), the '898 patent makes no further mention of "Event 15". As shown in Table 4 of the '898 patent, for Event 15, the capture detection circuit had a success rate index of less than one for three of the six pacing settings tested (col. 28, ll. 36-40). Therefore, the '898 patent suggests that ring-to-can sensing is not beneficial for detection of ventricular evoked responses.

None of the aforementioned patents discuss an atrial pacing and sensing system that diminishes and/or eliminates the effects of electrode polarization through electrode configuration. In particular, none of the aforementioned patents disclose an atrial pacing and sensing system wherein detection of an atrial evoked response occurs more than approximately 20 milliseconds after administration of an atrial pulse and/or wherein an atrial evoked response is relatively independent of pulse power.

SUMMARY

A method for sensing cardiac activity in a right atrium of a patient's heart that includes delivering a pulse to the right atrium and sensing cardiac activity in the right atrium using a unipolar electrode configuration to provide a sensed signal wherein the unipolar electrode configuration optionally uses an anode electrode of the delivered pulse. According to this method, an implantable pacing device optionally uses the sensed signal and/or sensing to determine whether an atrial evoked response occurred in response to the delivered pulse. In one exemplary method, pacing uses a bipolar electrode configuration that includes a tip and a ring electrode and sensing uses a unipolar electrode configuration that includes the ring electrode. The various systems and methods described herein, and equivalents thereof, are suitable for use in a variety of pacing therapies and other cardiac related therapies.

BRIEF DESCRIPTION OF THE DRAWINGS

Features and advantages of the described implementations can be more readily understood by reference to the following description taken in conjunction with the accompanying drawings.

DETAILED DESCRIPTION

The following description is of the best mode presently contemplated for practicing the described implementations. This description is not to be taken in a limiting sense, but rather is made merely for the purpose of describing the general principles of the implementations. The scope of the described implementations should be ascertained with reference to the issued claims. In the description that follows, like numerals or reference designators will be used to reference like parts or elements throughout.

Exemplary Stimulation Device

The techniques described below are intended to be implemented in connection with any stimulation device that is configured or configurable to stimulate or shock a patient's heart.

Figure 1:
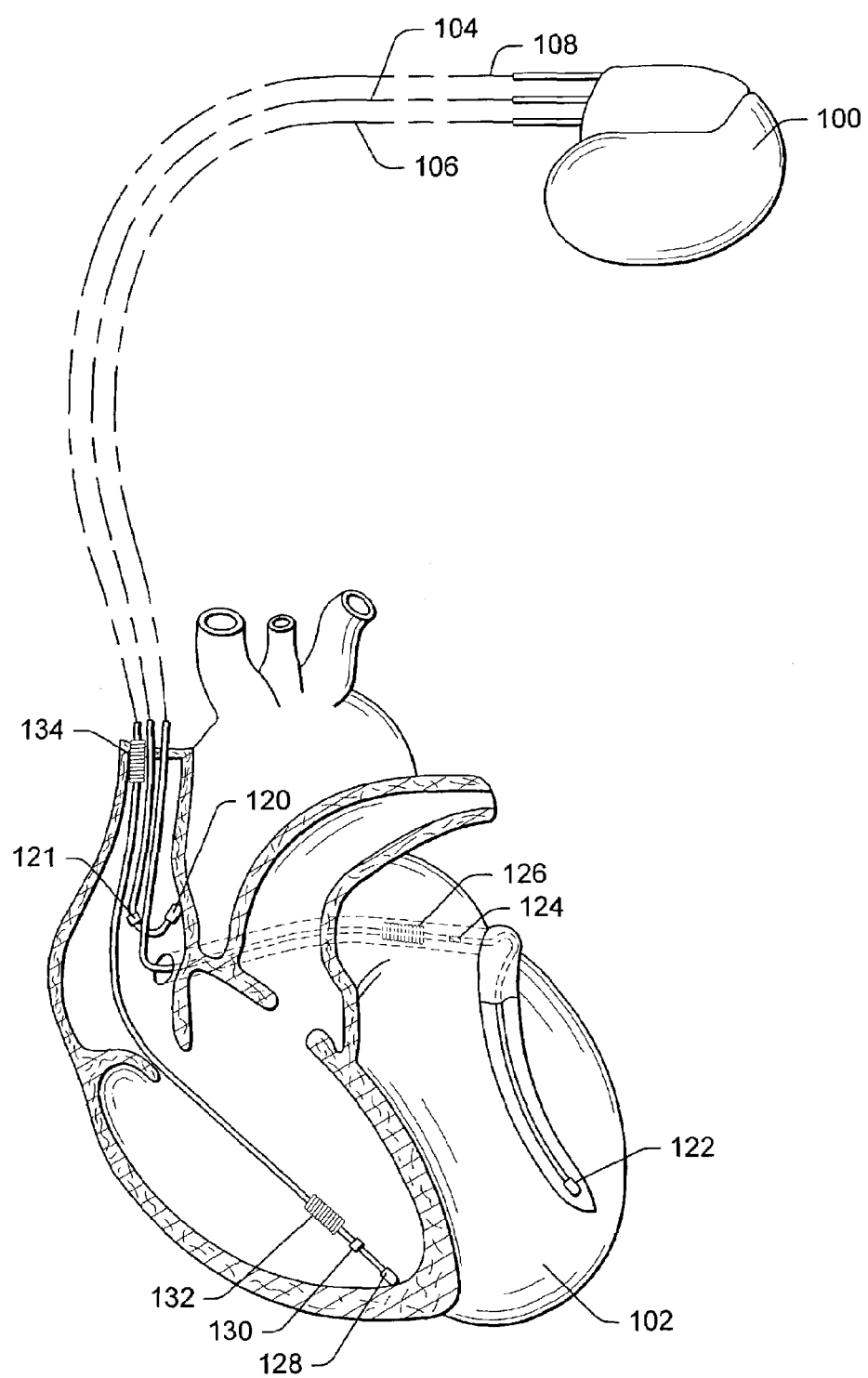
FIG. 1 is a simplified diagram illustrating an implantable stimulation device in electrical communication with at least three leads implanted into a patient's heart for delivering multi-chamber stimulation and shock therapy.

FIG. 1 shows an exemplary stimulation device 100 in electrical communication with a patient's heart 102 by way of three leads 104, 106, and 108, suitable for delivering multi-chamber stimulation and shock therapy. To sense atrial cardiac signals and to provide right atrial chamber stimulation therapy, stimulation device 100 is coupled to an implantable right atrial lead 104 having at least an atrial tip electrode 120, which typically is implanted in the patient's right atrial appendage. The right atrial lead 104, as shown in FIG. 1, also includes an atrial ring electrode 121, which is typically implanted in the patient's right atrial appendage. The atrial tip electrode 120 and the atrial ring electrode 121, as located on the right atrial lead 104, allow for bipolar pacing and/or sensing in a patient's right atrium. In addition, the atrial tip electrode 120 or the atrial ring electrode 121 allow for unipolar pacing and/or sensing between either the atrial tip electrode 120 and the stimulation device 100 or the atrial ring electrode 121 and the stimulation device 100.

In general, a bipolar lead has two electrical poles (e.g., a negative pole and a positive pole) that are connected to and located at a distance from a stimulation device. For example, a negative pole (or cathode) may be a tip electrode (e.g., the tip electrode 120) located at a distal end of a lead, while a positive pole (or anode) may be an annular electrode (e.g., the ring electrode 121) located several millimeters proximal to the tip electrode. Of course, a stimulation device may use a bipolar configuration having a reverse polarity, i.e., tip anode and ring cathode.

Electrodes suitable for use with the various exemplary systems and/or methods described herein include chemically and/or physically treated (e.g., coated, modified, etc.) electrodes wherein such treatment increases micro surface area of the treated electrode. Suitable electrodes include, for example, a titanium nitride material as a porous conductive material which increases the surface area on a microscopic scale. In general, suitable electrodes include those having micron and/or sub-micron surface features, for example, sputtered, sintered or otherwise produced porous metal, metal oxide or metal nitride coatings, including platinum, iridium, titanium, iridium oxide, tantalum oxide, iridium nitride and the like. Further, plasma cleaned electrodes are suitable.

As described with reference to FIG. 2, the stimulation device 100 includes a housing, often referred to as the "can", "case" or "case electrode", that may be programmably selected to act as an electrode for "unipolar" modes. Of course, a separate electrode (or electrodes), located on or near the housing, may also provide for similar operational modes, which are referred to herein as "unipolar" modes as well. Thus, a unipolar atrial electrode configuration uses the pacing device can as an electrode and/or an electrode (or electrodes) located on or near the can; whereas, a bipolar atrial electrode configuration uses two electrodes located in and/or near a patient's atrium.

To sense left atrial and ventricular cardiac signals and to provide left chamber pacing therapy, stimulation device 100 is coupled to a coronary sinus lead 106 designed for placement in the coronary sinus region via the coronary sinus for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 106 is designed to receive atrial and ventricular cardiac signals and to deliver left ventricular pacing therapy using at least a left ventricular tip electrode 122, left atrial pacing therapy using at least a left atrial ring electrode 124, and shocking therapy using at least a left atrial coil electrode 126. For a complete description of a coronary sinus lead, the reader is directed to U.S. patent application Ser. No. 09/457,277, filed Dec. 8, 1999, entitled "A Self-Anchoring, Steerable Coronary Sinus Lead" (Pianca et al.); and U.S. Pat. No. 5,466,254, "Coronary Sinus Lead with Atrial Sensing Capability" (Helland), which are incorporated herein by reference.

Stimulation device 100 is also shown in electrical communication with the patient's heart 102 by way of an implantable right ventricular lead 108 having, in this implementation, a right ventricular tip electrode 128, a right ventricular ring electrode 130, a right ventricular (RV) coil electrode 132, and an SVC coil electrode 134. Typically, the right ventricular lead 108 is transvenously inserted into the heart 102 to place the right ventricular tip electrode 128 in the right ventricular apex so that the RV coil electrode 132 will be positioned in the right ventricle and the SVC coil electrode 134 will be positioned in the superior vena cava. Accordingly, the right ventricular lead 108 is capable of sensing or receiving cardiac signals, and delivering stimulation in the form of pacing and shock therapy to the right ventricle.

Figure 2:
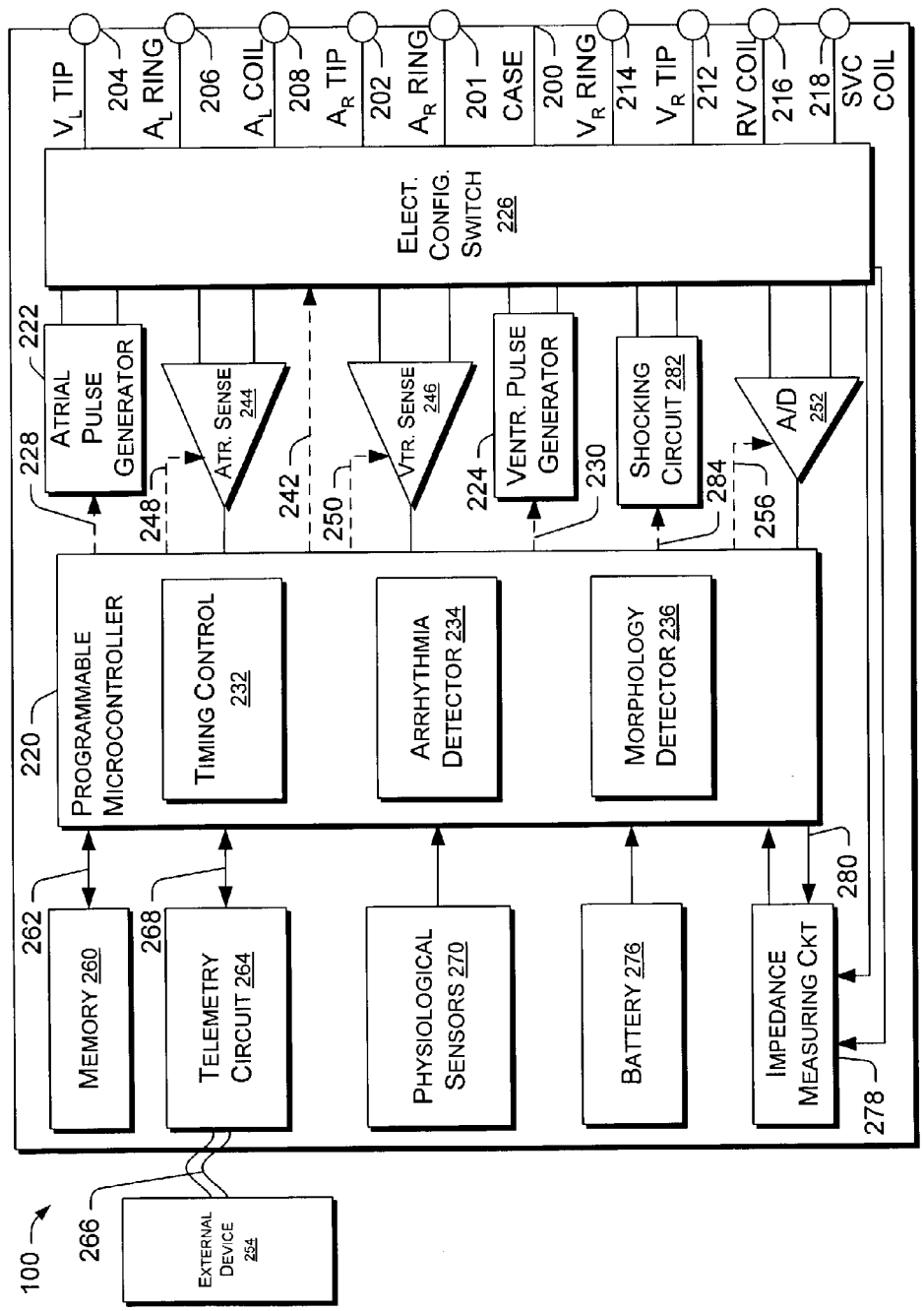
FIG. 2 is a functional block diagram of a multi-chamber implantable stimulation device illustrating basic elements that are configured to provide cardioversion, defibrillation, and pacing stimulation in four chambers of the heart. The implantable stimulation device is further configured to sense information and administer stimulation pulses responsive to such information.

FIG. 2 shows an exemplary, simplified block diagram depicting various components of stimulation device 100. The stimulation device 100 can be capable of treating both fast and slow arrhythmias with stimulation therapy, including cardioversion, defibrillation, and pacing stimulation. While a particular multi-chamber device is shown, it is to be appreciated and understood that this is done for illustration purposes only. Thus, the techniques and methods described below can be implemented in connection with any suitably configured or configurable stimulation device. Accordingly, one of skill in the art could readily duplicate, eliminate, or disable the appropriate circuitry in any desired combination to provide a device capable of treating the appropriate chamber(s) with cardioversion, defibrillation, and pacing stimulation.

Housing 200 for stimulation device 100 is often referred to as the "can", "case" or "case electrode", and may be programmably selected to act as the return electrode for all "unipolar" modes. Housing 200 may further be used as a return electrode alone or in combination with one or more of the coil electrodes 126, 132 and 134 for shocking purposes. Housing 200 further includes a connector (not shown) having a plurality of terminals 202, 204, 206, 208, 212, 214, 216, and 218 (shown schematically and, for convenience, the names of the electrodes to which they are connected are shown next to the terminals).

To achieve right atrial sensing and pacing, the connector includes at least a right atrial tip terminal ($A_R$ TIP) 202 adapted for connection to the atrial tip electrode 120. In addition, the connector includes at least a right atrial ring terminal ($A_R$ RING) 201 (or other terminal to allow for bipolar pacing in a right atrium) adapted for connection to a right atrial ring electrode 121 (or other right atrial electrode).

To achieve left chamber sensing, pacing, and shocking, the connector includes at least a left ventricular tip terminal ($V_L$ TIP) 204, a left atrial ring terminal ($A_L$ RING) 206, and a left atrial shocking terminal ($A_L$ COIL) 208, which are adapted for connection to the left ventricular tip electrode 122, the left atrial ring electrode 124, and the left atrial coil electrode 126, respectively.

To support right chamber sensing, pacing, and shocking, the connector further includes a right ventricular tip terminal ($V_R$ TIP) 212, a right ventricular ring terminal ($V_R$ RING) 214, a right ventricular shocking terminal (RV COIL) 216, and a superior vena cava shocking terminal (SVC COIL) 218, which are adapted for connection to the right ventricular tip electrode 128, right ventricular ring electrode 130, the RV coil electrode 132, and the SVC coil electrode 134, respectively.

At the core of the stimulation device 100 is a programmable microcontroller 220 that controls the various modes of stimulation therapy. As is well known in the art, microcontroller 220 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, microcontroller 220 includes the ability to process or monitor input signals (data or information) as controlled by a program code stored in a designated block of memory. The type of microcontroller is not critical to the described implementations. Rather, any suitable microcontroller 220 may be used that carries out the functions described herein. The use of microprocessor-based control circuits for performing timing and data analysis functions are well known in the art.

Representative types of control circuitry that may be used in connection with the described embodiments can include the microprocessor-based control system of U.S. Pat. No. 4,940,052 (Mann et al.); the state-machine of U.S. Pat. Nos. 4,712,555 (Thornander et al.); and 4,944,298 (Sholder), all of which are incorporated by reference herein. For a more detailed description of the various timing intervals used within the stimulation device and their inter-relationship, see U.S. Pat. No. 4,788,980 (Mann et al.), also incorporated herein by reference.

FIG. 2 also shows an atrial pulse generator 222 and a ventricular pulse generator 224 that generate pacing stimulation pulses for delivery by the right atrial lead 104, the coronary sinus lead 106, and/or the right ventricular lead 108 via an electrode configuration switch 226. It is understood that in order to provide stimulation therapy in each of the four chambers of the heart, the atrial and ventricular pulse generators, 222 and 224, may include dedicated, independent pulse generators, multiplexed pulse generators, or shared pulse generators. The pulse generators 222 and 224 are controlled by the microcontroller 220 via appropriate control signals 228 and 230, respectively, to trigger or inhibit the stimulation pulses.

Microcontroller 220 further includes timing control circuitry 232 to control the timing of the stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art.

Microcontroller 220 further includes an arrhythmia detector 234, a morphology detector 236, and optionally an orthostatic compensator and a minute ventilation (MV) response module, the latter two are not shown in FIG. 2. These components can be utilized by the stimulation device 100 for determining desirable times to administer various therapies, including those to reduce the effects of orthostatic hypotension. The aforementioned components may be implemented in hardware as part of the microcontroller 220, or as software/firmware instructions programmed into the device and executed on the microcontroller 220 during certain modes of operation.

The electronic configuration switch 226 includes a plurality of switches for connecting the desired electrodes to the appropriate I/O circuits, thereby providing complete electrode programmability. Accordingly, switch 226, in response to a control signal 242 from the microcontroller 220, determines the polarity of the stimulation pulses (e.g., unipolar, bipolar, combipolar, etc.) by selectively closing the appropriate combination of switches (not shown) as is known in the art.

Atrial sensing circuits 244 and ventricular sensing circuits 246 may also be selectively coupled to the right atrial lead 104, coronary sinus lead 106, and the right ventricular lead 108, through the switch 226 for detecting the presence of cardiac activity in each of the four chambers of the heart. Accordingly, the atrial (ATR. SENSE) and ventricular (VTR. SENSE) sensing circuits, 244 and 246, may include dedicated sense amplifiers, multiplexed amplifiers, or shared amplifiers. Switch 226 determines the "sensing polarity" of the cardiac signal by selectively closing the appropriate switches, as is also known in the art. In this way, the clinician may program the sensing polarity independent of the stimulation polarity. The sensing circuits (e.g., 244 and 246) are optionally capable of obtaining information indicative of tissue capture.

Each sensing circuit 244 and 246 preferably employs one or more low power, precision amplifiers with programmable gain and/or automatic gain control, bandpass filtering, and a threshold detection circuit, as known in the art, to selectively sense the cardiac signal of interest. The automatic gain control enables the device 100 to deal effectively with the difficult problem of sensing the low amplitude signal characteristics of atrial or ventricular fibrillation.

The outputs of the atrial and ventricular sensing circuits 244 and 246 are connected to the microcontroller 220, which, in turn, is able to trigger or inhibit the atrial and ventricular pulse generators 222 and 224, respectively, in a demand fashion in response to the absence or presence of cardiac activity in the appropriate chambers of the heart. Furthermore, as described herein, the microcontroller 220 is also capable of analyzing information output from the sensing circuits 244 and 246 and/or the data acquisition system 252 to determine or detect whether and to what degree tissue capture has occurred and to program a pulse, or pulses, in response to such determinations. The sensing circuits 244 and 246, in turn, receive control signals over signal lines 248 and 250 from the microcontroller 220 for purposes of controlling the gain, threshold, polarization charge removal circuitry (not shown), and the timing of any blocking circuitry (not shown) coupled to the inputs of the sensing circuits, 244 and 246, as is known in the art.

For arrhythmia detection, the device 100 utilizes the atrial and ventricular sensing circuits, 244 and 246, to sense cardiac signals to determine whether a rhythm is physiologic or pathologic. In reference to arrhythmias, as used herein, "sensing" is reserved for the noting of an electrical signal or obtaining data (information), and "detection" is the processing (analysis) of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the arrhythmia detector 234 of the microcontroller 220 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to inputs of an analog-to-digital (A/D) data acquisition system 252. The data acquisition system 252 is configured to acquire intracardiac electrogram signals, convert the raw analog data into a digital signal, and store the digital signals for later processing and/or telemetric transmission to an external device 254. The data acquisition system 252 is coupled to the right atrial lead 104, the coronary sinus lead 106, and the right ventricular lead 108 through the switch 226 to sample cardiac signals across any pair of desired electrodes.

The microcontroller 220 is further coupled to a memory 260 by a suitable data/address bus 262, wherein the programmable operating parameters used by the microcontroller 220 are stored and modified, as required, in order to customize the operation of the stimulation device 100 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 102 within each respective tier of therapy. One feature of the described embodiments is the ability to sense and store a relatively large amount of data (e.g., from the data acquisition system 252), which data may then be used for subsequent analysis to guide the programming of the device.

Advantageously, the operating parameters of the implantable device 100 may be non-invasively programmed into the memory 260 through a telemetry circuit 264 in telemetric communication via communication link 266 with the external device 254, such as a programmer, transtelephonic transceiver, or a diagnostic system analyzer. The microcontroller 220 activates the telemetry circuit 264 with a control signal 268. The telemetry circuit 264 advantageously allows intracardiac electrograms and status information relating to the operation of the device 100 (as contained in the microcontroller 220 or memory 260) to be sent to the external device 254 through an established communication link 266.

The stimulation device 100 can further include a physiologic sensor 270, commonly referred to as a "rate-responsive" sensor because it is typically used to adjust pacing stimulation rate according to the exercise state of the patient. However, the physiological sensor 270 may further be used to detect changes in cardiac output, changes in the physiological condition of the heart, or diurnal changes in activity (e.g., detecting sleep and wake states). Accordingly, the microcontroller 220 responds by adjusting the various pacing parameters (such as rate, AV Delay, V-V Delay, etc.) at which the atrial and ventricular pulse generators, 222 and 224, generate stimulation pulses.

While shown as being included within the stimulation device 100, it is to be understood that the physiologic sensor 270 may also be external to the stimulation device 100, yet still be implanted within or carried by the patient. Examples of physiologic sensors that may be implemented in device 100 include known sensors that, for example, sense respiration rate, pH of blood, ventricular gradient, and so forth. Another sensor that may be used is one that detects activity variance, wherein an activity sensor is monitored diurnally to detect the low variance in the measurement corresponding to the sleep state. For a complete description of the activity variance sensor, the reader is directed to U.S. Pat. No. 5,476,483 (Bornzin et. al), issued Dec. 19, 1995, which patent is hereby incorporated by reference.

More specifically, the physiological sensors 270 optionally include sensors for detecting movement and minute ventilation in the patient. The physiological sensors 270 may include a position sensor and/or a minute ventilation (MV) sensor to sense minute ventilation, which is defined as the total volume of air that moves in and out of a patient's lungs in a minute. Signals generated by the position sensor and MV sensor are passed to the microcontroller 220 for analysis in determining whether to adjust the pacing rate, etc. The microcontroller 220 monitors the signals for indications of the patient's position and activity status, such as whether the patient is climbing upstairs or descending downstairs or whether the patient is sitting up after lying down.

The stimulation device additionally includes a battery 276 that provides operating power to all of the circuits shown in FIG. 2. For the stimulation device 100, which employs shocking therapy, the battery 276 is capable of operating at low current drains for long periods of time (e.g., preferably less than 10 µA), and is capable of providing high-current pulses (for capacitor charging) when the patient requires a shock pulse (e.g., preferably, in excess of 2 A, at voltages above 2 V, for periods of 10 seconds or more). The battery 276 also desirably has a predictable discharge characteristic so that elective replacement time can be detected.

The stimulation device 100 can further include magnet detection circuitry (not shown), coupled to the microcontroller 220, to detect when a magnet is placed over the stimulation device 100. A magnet may be used by a clinician to perform various test functions of the stimulation device 100 and/or to signal the microcontroller 220 that the external programmer 254 is in place to receive or transmit data to the microcontroller 220 through the telemetry circuits 264.

The stimulation device 100 further includes an impedance measuring circuit 278 that is enabled by the microcontroller 220 via a control signal 280. The known uses for an impedance measuring circuit 278 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 278 is advantageously coupled to the switch 226 so that any desired electrode may be used.

In the case where the stimulation device 100 is intended to operate as an implantable cardioverter/defibrillator (ICD) device, it detects the occurrence of an arrhythmia, and automatically applies an appropriate therapy to the heart aimed at terminating the detected arrhythmia. To this end, the microcontroller 220 further controls a shocking circuit 282 by way of a control signal 284. The shocking circuit 282 generates shocking pulses of low (up to 0.5 J), moderate (0.5 J to 10 J), or high energy (10 J to 40 J), as controlled by the microcontroller 220. Such shocking pulses are applied to the patient's heart 102 through at least two shocking electrodes, and as shown in this embodiment, selected from the left atrial coil electrode 126, the RV coil electrode 132, and/or the SVC coil electrode 134. As noted above, the housing 200 may act as an active electrode in combination with the RV electrode 132, or as part of a split electrical vector using the SVC coil electrode 134 or the left atrial coil electrode 126 (i.e., using the RV electrode as a common electrode).

Cardioversion level shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5 J to 40 J), delivered asynchronously (since R-waves may be too disorganized), and pertaining exclusively to the treatment of fibrillation. Accordingly, the microcontroller 220 is capable of controlling the synchronous or asynchronous delivery of the shocking pulses.

Figure 3:
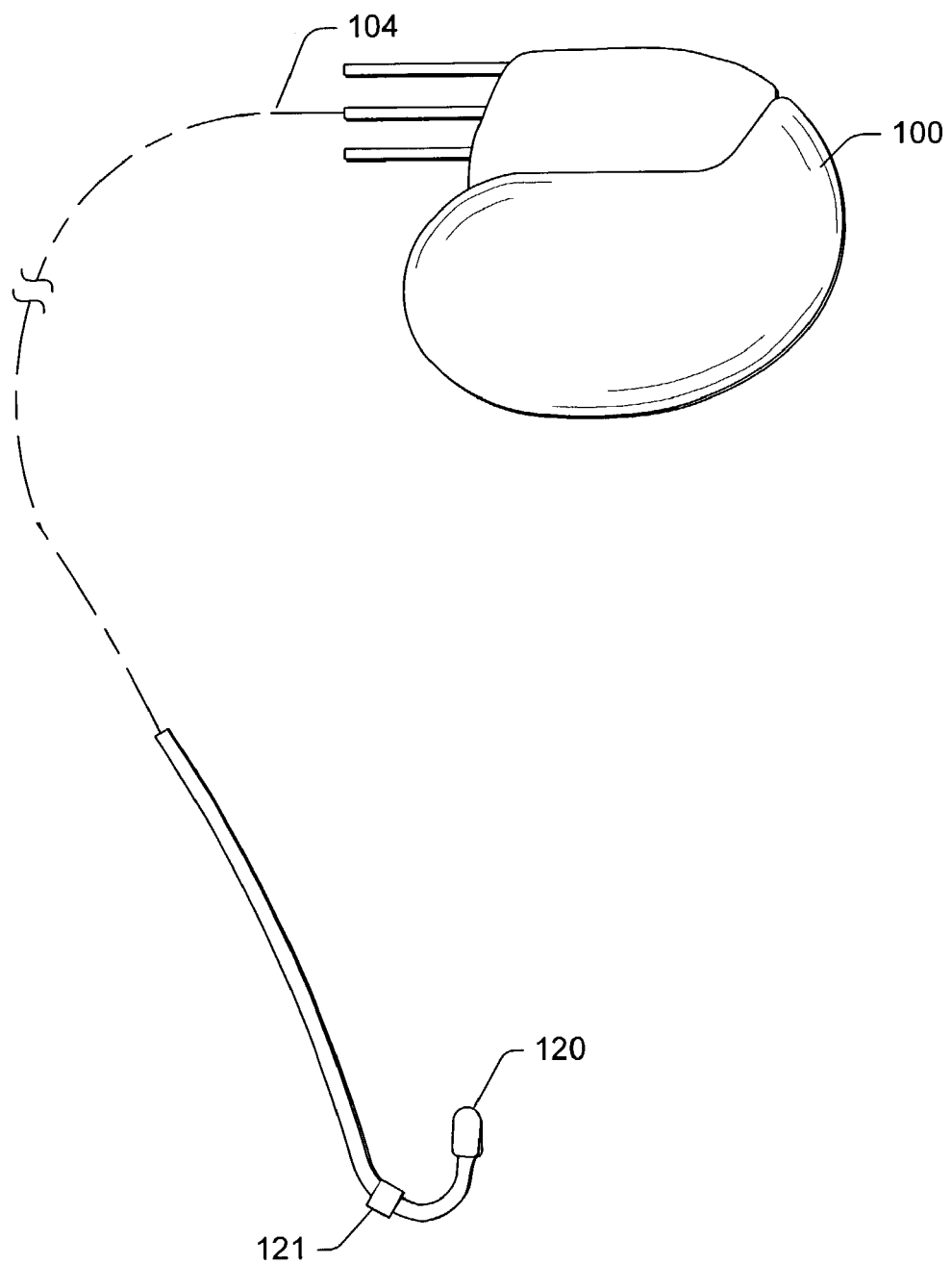
FIG. 3 is a simplified diagram illustrating the implantable stimulation device of FIG. 1 in electrical communication with an implantable lead for implantation into a patient's heart for delivering pacing pulses and sensing cardiac activity.

Referring to FIG. 3, an exemplary system including an implantable pacing device 100 and an atrial lead 104 is shown. The atrial lead 104 includes two separate electrodes: an atrial tip electrode 120 and an atrial ring electrode 121. The implantable pacing device 100 includes various hardware and software as described with reference to FIG. 2. Through use of such hardware and software, the exemplary system of FIG. 3 is capable of performing bipolar atrial pacing and unipolar atrial sensing.

Figure 4:
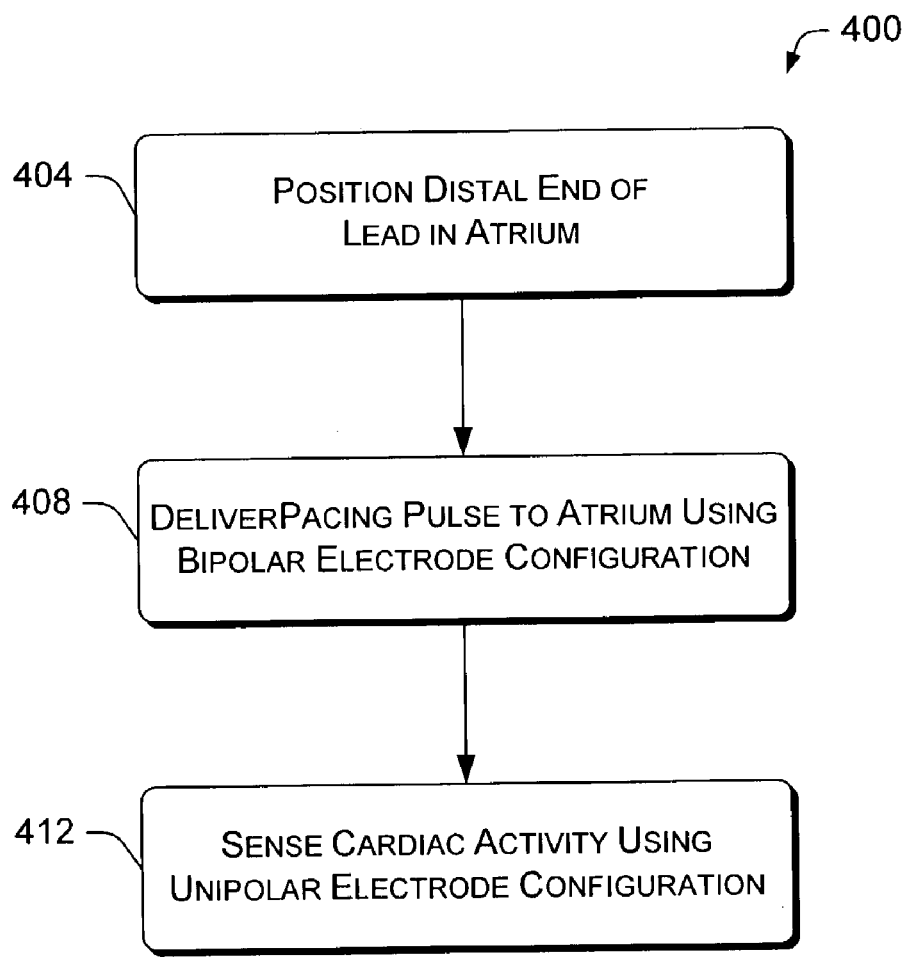
FIG. 4 is a block diagram of an exemplary method for atrial pacing and sensing.

Referring to FIG. 4, a block diagram of an exemplary method for atrial pacing and sensing 400 is shown. In a positioning block 404, a lead (e.g., the lead 104 of FIGS. 1-3) is positioned in an atrium of a patient's heart. According to this exemplary method 400, the lead includes at least two electrodes to allow for delivery of a bipolar pacing pulse. In a delivery block 408, an implantable pacing device, in electrical communication with the lead, delivers a pacing pulse using a bipolar electrode configuration. For example, with reference to the lead 104 shown in FIG. 3, the bipolar electrode configuration optionally includes electrodes such as the atrial tip electrode 120 and the atrial ring electrode 121. A sense block 412 follows the delivery block 408 wherein the implantable pacing device senses cardiac activity using a unipolar electrode configuration. For example, with reference to the lead 104 and implantable pacing device 100 shown in FIG. 3, the unipolar electrode configuration optionally includes at least one of the lead electrodes 120, 121 and the can of the implantable pacing device 100.

Figure 5:
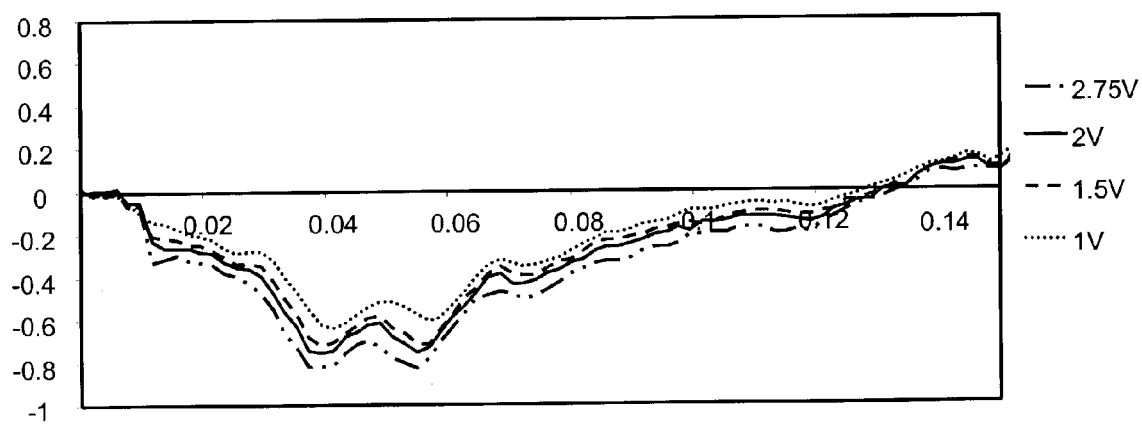
FIG. 5 is a plot of cardiac activity with respect to time sensed in a patient using a unipolar electrode configuration.

Referring to FIGS. 5 through 9, exemplary plots of voltage versus time are shown for data collected from five different patients. The patients were fitted with bipolar atrial stimulation leads having coated electrodes, specifically electrodes having titanium nitride as a material of construction. Data shown in the plots of FIGS. 5 through 9 correspond to cardiac activity sensed using a unipolar ring and case electrode configuration following delivery of an atrial pacing pulse using a bipolar electrode configuration. The plot of FIG. 5 shows cardiac activity corresponding to atrial pacing pulses that were delivered at four different voltage levels: 1V, 1.5 V, 2 V, and 2.75 V. Three pulses were delivered at a voltage level of 0.75 V using a bipolar electrode configuration; however, the pulses at this voltage level did not cause an atrial evoked response. For the higher voltage levels, equal to and greater than approximately 1 V, the pulses did cause atrial evoked responses. The voltage versus time data, as sensed using a unipolar ring electrode to case configuration, indicate that the atrial evoked response is relatively independent of pulse voltage for voltage level of approximately 1 V to approximately 2.75 V. On the basis of these data, one of ordinary skill in the art would expect that the even higher pulse voltage levels would not cause any significant deviation that would obscure the form and amplitude of the atrial evoked response. Thus, an exemplary method using a bipolar configuration for atrial pacing and a unipolar configuration for atrial sensing (e.g., the method 400 of FIG. 4), produces a relatively repeatable atrial evoked response that is also relatively independent of pulse voltage levels. Alternatively, such an exemplary method uses a unipolar electrode configuration for pacing and a unipolar ring and case electrode configuration for sensing.

The atrial evoked responses shown in FIG. 5, for pulse voltage levels equal to and greater than approximately 1 V, have a similar time response. At these bipolar pulse voltage levels, the corresponding atrial evoked response voltage, sensed using a unipolar ring and case electrode configuration, becomes negative within approximately 10 milliseconds after pulse administration. Further, the evoked response voltage reaches a first minimum approximately 40 milliseconds after pulse administration and reaches a second minimum approximately 55 milliseconds after pulse administration. Thereafter, the evoked response voltage increases and reaches a null voltage at approximately 130 milliseconds after pulse administration. For the pulse voltages that did not cause an evoked response, the unipolar ring and case electrode configuration registered a relatively constant voltage, which for practical purposes, is referred to herein as a DC voltage.

Figure 6:
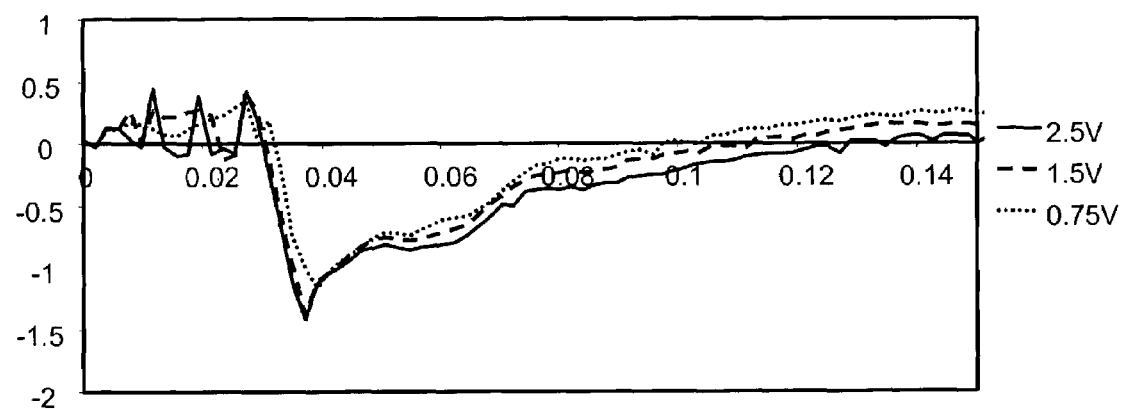
FIG. 6 is a plot of cardiac activity with respect to time sensed in another patient using a unipolar electrode configuration.

The plot of FIG. 6 shows cardiac activity corresponding to atrial pacing pulses that were delivered at three different voltage levels: 0.75 V, 1.5 V, and 2.5 V. Four pulses were delivered at a voltage level of 0.5 V using a bipolar electrode configuration; however, pulses at this voltage level did not cause an atrial evoked response. For the higher voltage levels, equal to and greater than approximately 0.75 V, the pulses did cause atrial evoked responses. The voltage versus time data, as sensed using a unipolar ring and case electrode configuration, indicate that the atrial evoked response is relatively independent of pulse voltage for voltage level of approximately 0.75 V to approximately 2.5 V. On the basis of these data, one of ordinary skill in the art would expect that the even higher pulse voltage levels would not cause any significant deviation that would obscure the form and amplitude of the atrial evoked response. Thus, an exemplary method using bipolar atrial pacing and unipolar atrial ring and case sensing (e.g., the exemplary method 400 of FIG. 4), produces a relatively repeatable atrial evoked response that is also relatively independent of pulse voltage levels.

The atrial evoked responses shown in FIG. 6, for pulse voltage levels equal to and greater than approximately 0.75 V, have a similar time response. At these bipolar pulse voltage levels, the corresponding atrial evoked response voltage, sensed using a unipolar ring and case electrode configuration, becomes negative within approximately 30 milliseconds after pulse administration. Further, the evoked response voltage reaches a minimum approximately 40 milliseconds after pulse administration. Thereafter, the evoked response voltage increases and reaches a null voltage at approximately 120 milliseconds after pulse administration. For the pulse voltages that did not cause an evoked response, the unipolar ring and case electrode configuration registered a relatively constant voltage, which for practical purposes, is referred to herein as a DC voltage.

Figure 7:
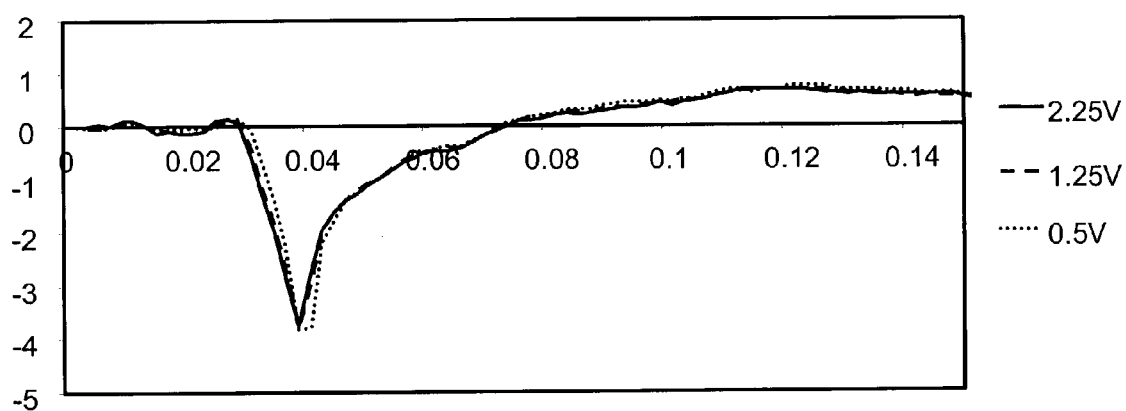
FIG. 7 is a plot of cardiac activity with respect to time sensed in yet another patient using a unipolar electrode configuration.

The plot of FIG. 7 shows cardiac activity corresponding to atrial pacing pulses that were delivered at three different voltage levels: 0.5 V, 1.25 V, and 2.25 V. Six pulses were delivered at a voltage level of 0.25 V using a bipolar electrode configuration; however, pulses at this voltage level did not cause an atrial evoked response. For the higher voltage levels, equal to and greater than approximately 0.5 V, the pulses did cause atrial evoked responses. The voltage versus time data, as sensed using a unipolar ring and case electrode configuration, indicate that the atrial evoked response is relatively independent of pulse voltage for voltage level of approximately 0.5 V to approximately 2.25 V. On the basis of these data, one of ordinary skill in the art would expect that the even higher pulse voltage levels would not cause any significant deviation that would obscure the form and amplitude of the atrial evoked response. Thus, an exemplary method using bipolar atrial pacing and unipolar atrial ring and case sensing (e.g., the exemplary method 400 of FIG. 4), produces a relatively repeatable atrial evoked response that is also relatively independent of pulse voltage levels.

The atrial evoked responses shown in FIG. 7, for pulse voltage levels equal to and greater than approximately 0.5 V, have a similar time response. At these bipolar pulse voltage levels, the corresponding atrial evoked response voltage, sensed using a unipolar ring and case electrode configuration, becomes negative within approximately 30 milliseconds after pulse administration. Further, the evoked response voltage reaches a minimum approximately 40 milliseconds after pulse administration. Thereafter, the evoked response voltage increases and reaches a null voltage at approximately 70 milliseconds after pulse administration. For the pulse voltages that did not cause an evoked response, the unipolar electrode ring and case configuration registered a relatively constant voltage, which for practical purposes, is referred to herein as a DC voltage.

Figure 8:
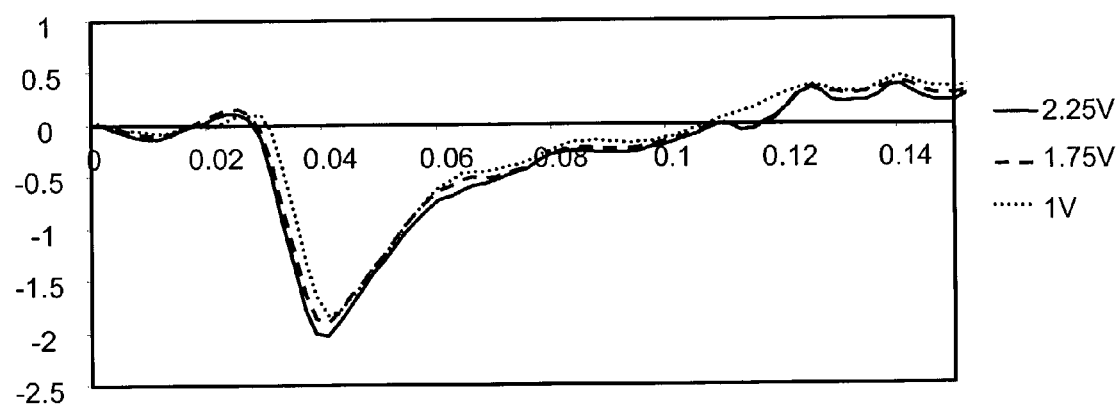
FIG. 8 is a plot of cardiac activity with respect to time sensed in yet another patient using a unipolar electrode configuration.

The plot of FIG. 8 shows cardiac activity corresponding to atrial pacing pulses that were delivered at three different voltage levels: 1V, 1.75 V, and 2.25 V. Five pulses were delivered at a voltage level of 0.75 V using a bipolar electrode configuration; however, pulses at this voltage level did not cause an atrial evoked response. For the higher voltage levels, equal to and greater than approximately 1 V, the pulses did cause atrial evoked responses. The voltage versus time data, as sensed using a unipolar ring and case electrode configuration, indicate that the atrial evoked response is relatively independent of pulse voltage for voltage level of approximately 1 V to approximately 2.25 V. On the basis of these data, one of ordinary skill in the art would expect that the even higher pulse voltage levels would not cause any significant deviation that would obscure the form and amplitude of the atrial evoked response. Thus, an exemplary method using bipolar atrial pacing and unipolar atrial ring and case sensing (e.g., the exemplary method 400 of FIG. 4), produces a relatively repeatable atrial evoked response that is also relatively independent of pulse voltage levels.

The atrial evoked responses shown in FIG. 8, for pulse voltage levels equal to and greater than approximately 1 V, have a similar time response. At these bipolar pulse voltage levels, the corresponding atrial evoked response voltage, sensed using a unipolar ring and case electrode configuration, becomes negative within approximately 30 milliseconds after pulse administration. Further, the evoked response voltage reaches a minimum approximately 40 milliseconds after pulse administration. Thereafter, the evoked response voltage increases and reaches a null voltage at approximately 110 milliseconds after pulse administration. For the pulse voltages that did not cause an evoked response, the unipolar ring and case electrode configuration registered a relatively constant voltage, which for practical purposes, is referred to herein as a DC voltage.

Figure 9:
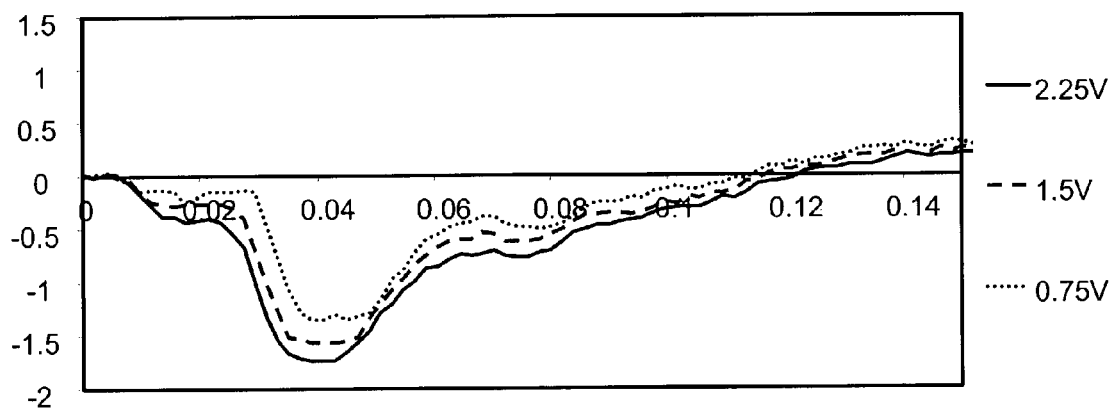
FIG. 9 is a plot of cardiac activity with respect to time sensed in yet another patient using a unipolar electrode configuration.

The plot of FIG. 9 shows cardiac activity corresponding to atrial pacing pulses that were delivered at three different voltage levels: 0.75 V, 1.5 V, and 2.25 V. Two pulses were delivered at a voltage level of 0.5 V using a bipolar electrode configuration; however, pulses at this voltage level did not cause an atrial evoked response. In one of the 0.5 V voltage pulses, starting at approximately 70 ms to approximately 80 ms following the atrial pacing pulse, an intrinsic P-wave, sensed in the unipolar ring and case configuration, occurred because the initial atrial pacing pulse did not capture. For the higher voltage levels, equal to and greater than approximately 0.75 V, the pulses did cause atrial evoked responses. The voltage versus time data, as sensed using a unipolar ring and case electrode configuration, indicate that the atrial evoked response is relatively independent of pulse voltage for voltage level of approximately 0.75 V to approximately 2.25 V. On the basis of these data, one of ordinary skill in the art would expect that the even higher pulse voltage levels would not cause any significant deviation that would obscure the form and amplitude of the atrial evoked response. Thus, an exemplary method using bipolar atrial pacing and unipolar atrial ring and case sensing (e.g., the exemplary method 400 of FIG. 4), produces a relatively repeatable atrial evoked response that is also relatively independent of pulse voltage levels.

The atrial evoked responses shown in FIG. 9, for pulse voltage levels equal to and greater than approximately 0.75 V, have a similar time response. At these bipolar pulse voltage levels, the corresponding atrial evoked response voltage, sensed using a unipolar ring and case electrode configuration, becomes negative within approximately 10 milliseconds after pulse administration. Further, the evoked response voltage reaches a minimum approximately 40 milliseconds after pulse administration. Thereafter, the evoked response voltage increases and reaches a null voltage at approximately 110 milliseconds after pulse administration. For the pulse voltages that did not cause an evoked response, the unipolar ring and case electrode configuration registered a relatively constant voltage, which for practical purposes, is referred to herein as a DC voltage.

Figure 10:
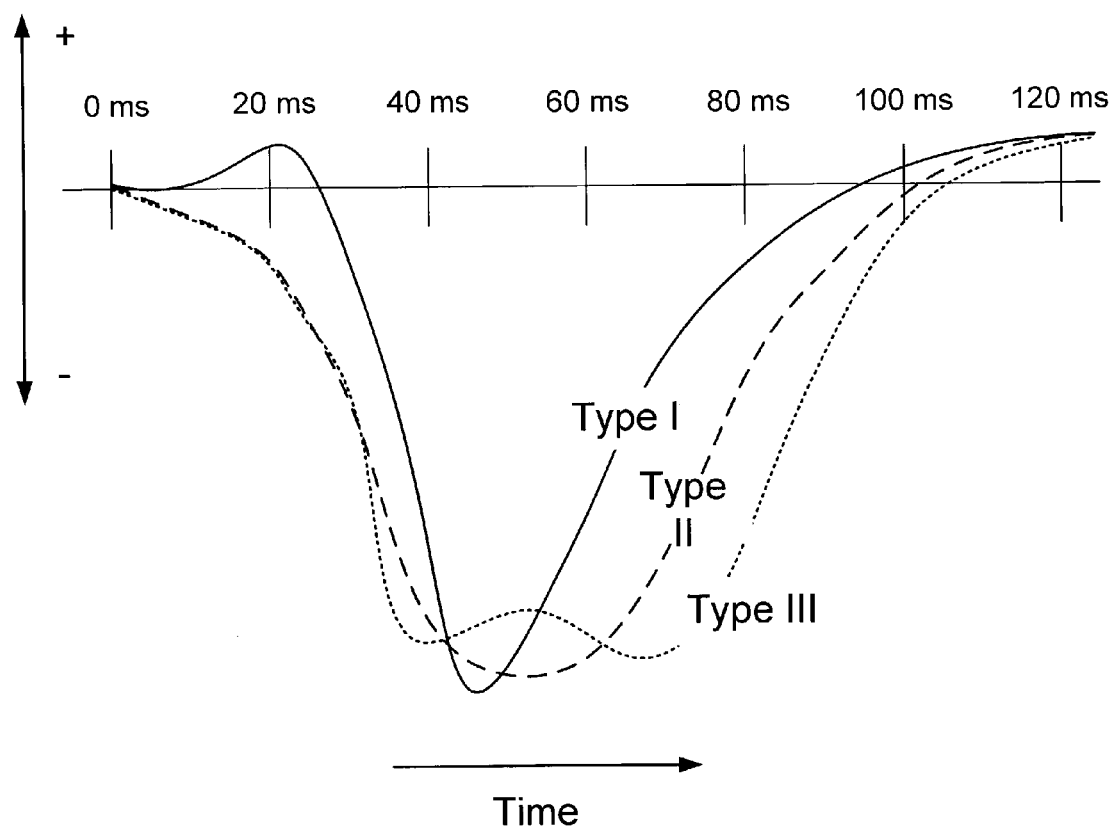
FIG. 10 is a diagrammatic plot of three generalized atrial evoked responses represented as voltage versus time.

Referring to FIGS. 5 through 9, the exemplary plots of voltage versus time, shown for data collected from five different patients, exhibit various characteristics. Some of these characteristics are patient dependent, while others are patient independent. Referring to FIG. 10, a plot of three exemplary atrial evoked responses is shown which exhibits various patient dependent and patient independent characteristics. These three non-limiting, exemplary atrial evoked responses, labeled Type I, Type II, and Type III, represent generalized characteristics taken from the data shown in the plots of FIGS. 5 through 9. While the data shown in FIGS. 5 through 9 was taken from only five different patients, one of ordinary skill in the art would expect that data taken from other patients would, in general, show similar characteristics.

Given the generalized responses shown in FIG. 10 (Type I, Type II, and Type III), a variety of exemplary detection methods are capable of detecting characteristics representative of an atrial evoked response. These exemplary detection methods include, but are not limited to, slope (or derivative), integral, amplitude (or threshold), and template (or fingerprint) methods, some of which are described with reference to FIGS. 11 through 16.

Figure 11:
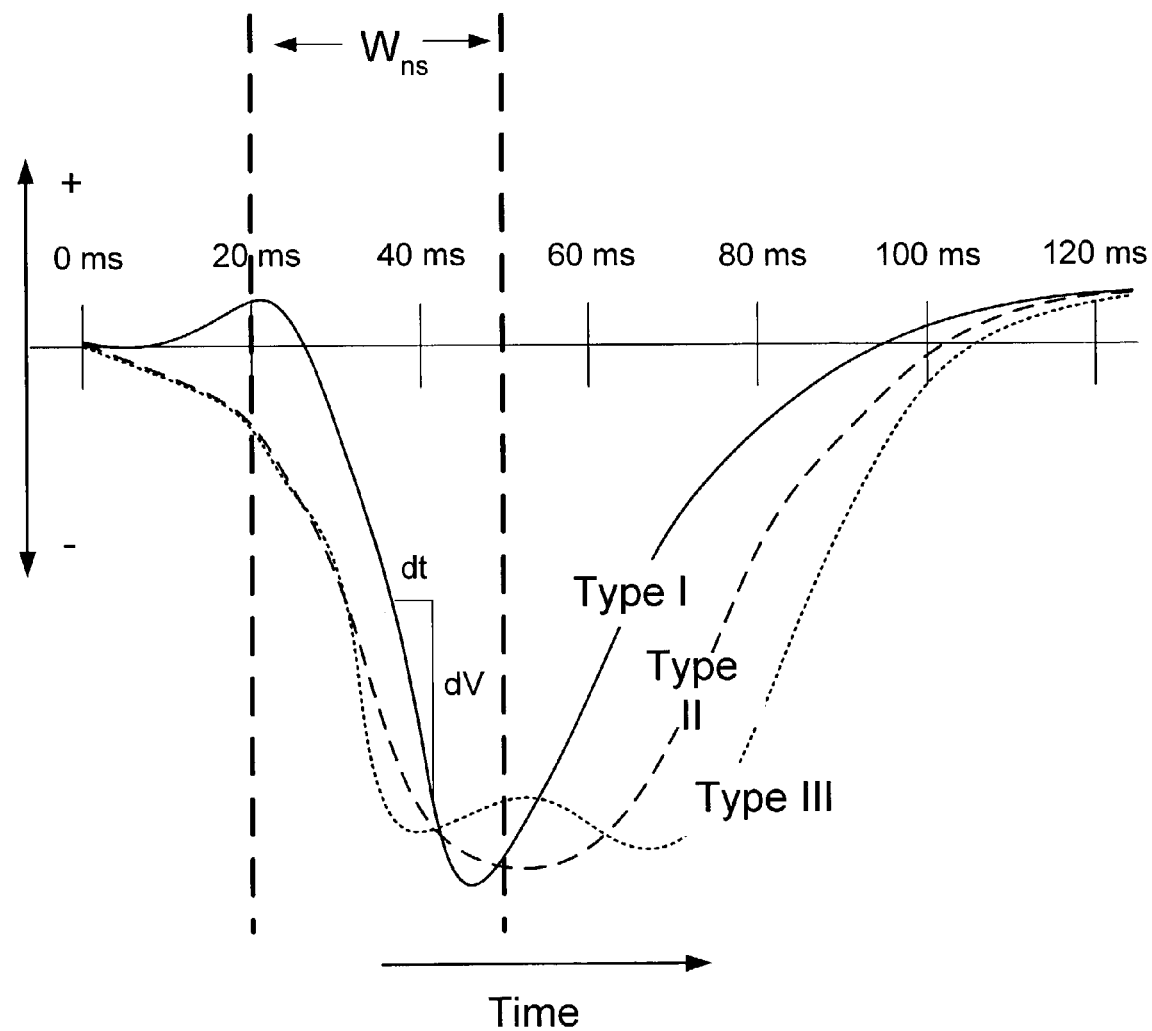
FIG. 11 is a diagrammatic plot, as shown in FIG. 10, further including a negative slope window.

Referring to FIG. 11, an exemplary negative slope time window ($W_{ns}$) is shown superimposed on the plot of FIG. 10. The negative slope time window ($W_{ns}$) begins at approximately 20 milliseconds and ends at approximately 50 milliseconds. At a post-pulse time of approximately 40 milliseconds, the Type I generalized atrial evoked response shows a time interval (dt) and a voltage interval (dV) representative of a derivative of the Type I evoked response. In particular, this corresponds to a maximum negative derivative (or slope) for the Type I response. Also note that the Type II and Type III responses also exhibit a maximum negative derivative (or slope) within the same window ($W_{ns}$).

Figure 12:
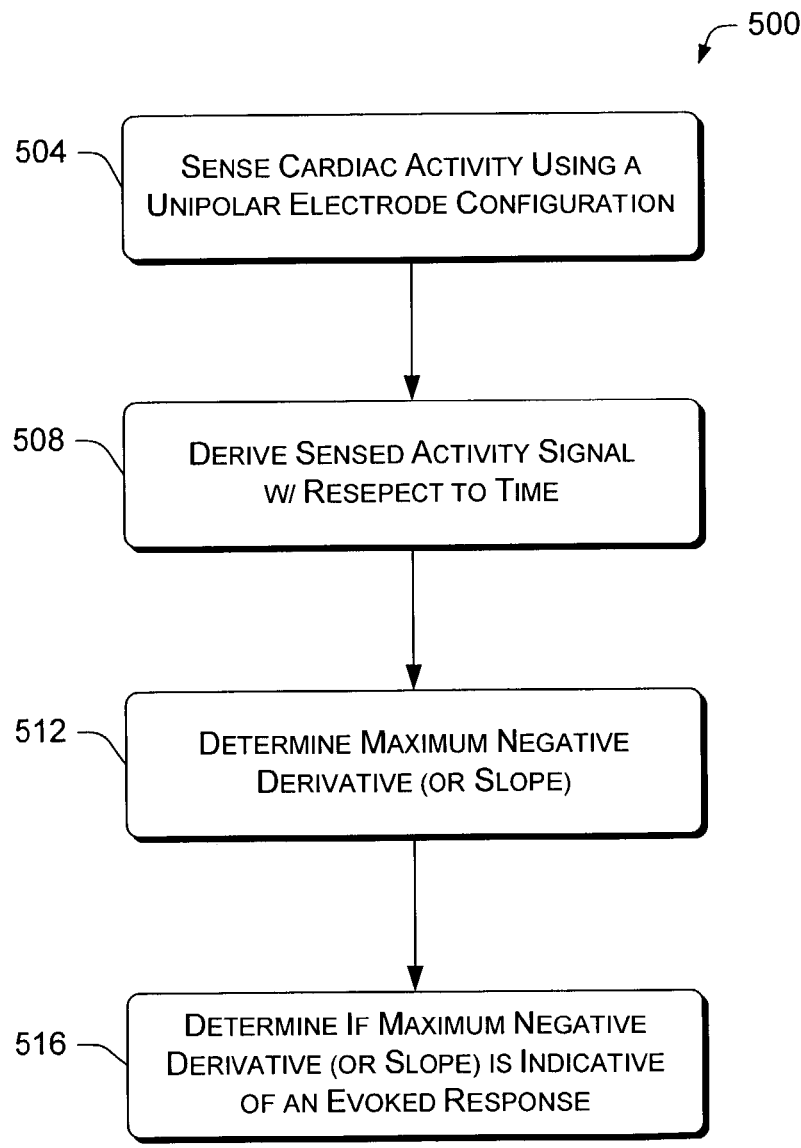
FIG. 12 is a block diagram of an exemplary method for detecting an atrial evoked response on the basis of a maximum negative derivative or slope.

An exemplary method for detecting an atrial evoked response 500 is shown in FIG. 12. In a sense block 504, an implantable pacing device (e.g., device 100 of FIGS. 1 and 2) senses cardiac activity using a unipolar electrode configuration (e.g., ring and case), typically after an atrial pacing pulse administered using a bipolar electrode configuration (or, alternatively, a unipolar electrode configuration) and in the form of an electrical signal. In a derivation block 508, the implantable pacing device determines a derivative of the sensed activity signal with respect to time. This derivative is optionally a smoothed or averaged value, made up of several sampled points, such that a prolonged negative slope will generate a relatively large value as opposed to, for example, a small value generated by a noisy, short signal deviation. Next, in a determination block 512, the implantable pacing device determines the maximum derivative of the sensed activity signal with respect to time for a time period commencing at or near an administered atrial pacing pulse or commencing approximately 10 milliseconds to 30 milliseconds after an administered bipolar atrial pacing pulse. In one example of the exemplary method 500, the time period commences at approximately 20 milliseconds after an administered bipolar atrial pacing pulse. In a second determination block 516, the implantable pacing device determines if the maximum negative derivative (or slope) is indicative of an atrial evoked response. The implantable pacing device optionally makes this determination by comparing the maximum negative derivative (or slope) to a parameter value. For example, if the maximum negative slope is −100 (arbitrary units of voltage over time) and the parameter value is −80 (arbitrary units of voltage over time), then the implantable pacing device determines that an atrial evoked response occurred. Following this determination, the implantable pacing device optionally terminates sensing and/or analysis of the unipolar atrial signal (e.g., sensed using a ring and case configuration) until delivery of a subsequent bipolar atrial pacing pulse (or, alternatively, a unipolar atrial pacing pulse).

Figure 13:
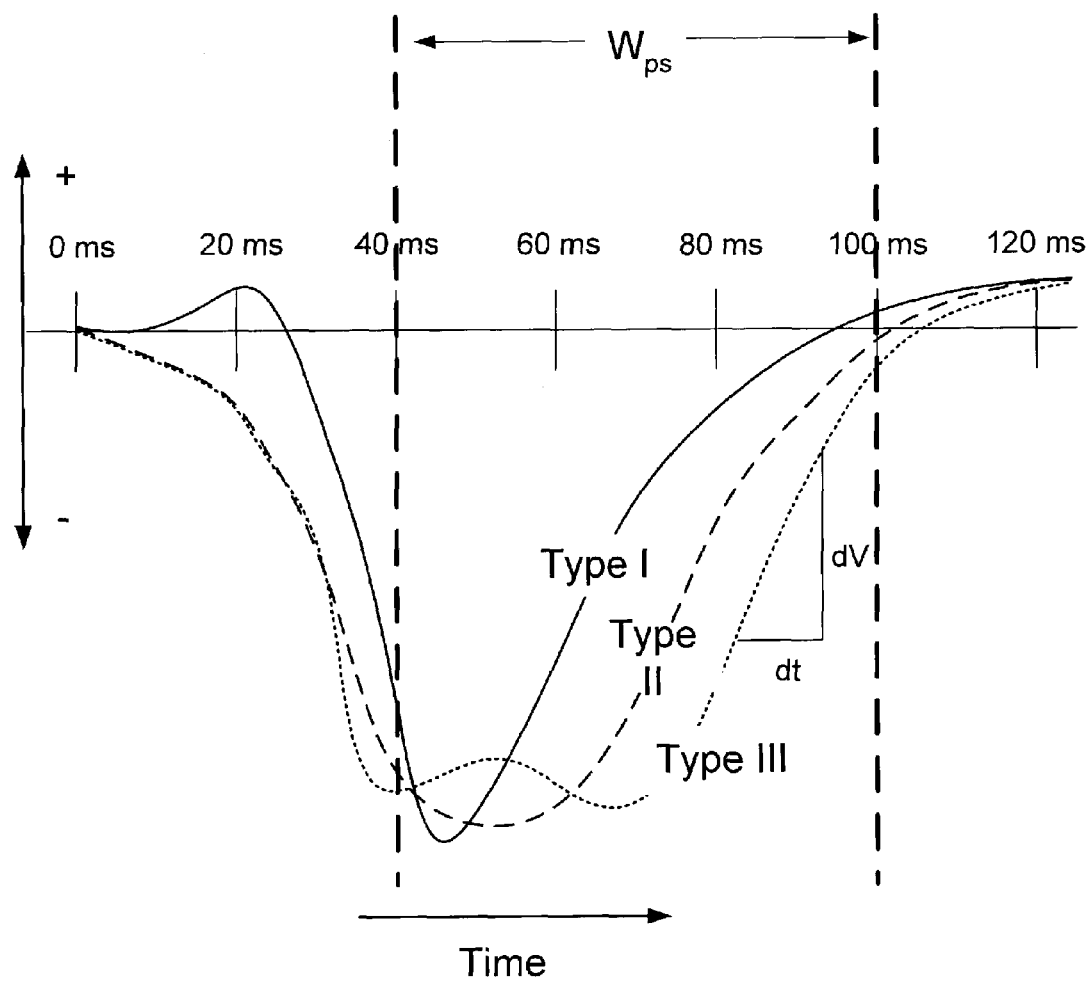
FIG. 13 is a diagrammatic plot, as shown in FIG. 10, further including a positive slope window.

Referring to FIG. 13, an exemplary positive slope time window ($W_{ps}$) is shown superimposed on the plot of FIG. 10. The positive slope time window ($W_{ps}$) begins at approximately 40 milliseconds and ends at approximately 100 milliseconds. At a post-pulse time of approximately 90 milliseconds, the Type II generalized atrial evoked response shows a time interval (dt) and a voltage interval (dV) representative of a derivative of the Type II evoked response. In particular, this corresponds to a maximum positive derivative (or slope) for the Type II response. Also note that the Type I and Type III responses also exhibit a maximum positive derivative (or slope) within the same window ($W_{ps}$).

Figure 14:
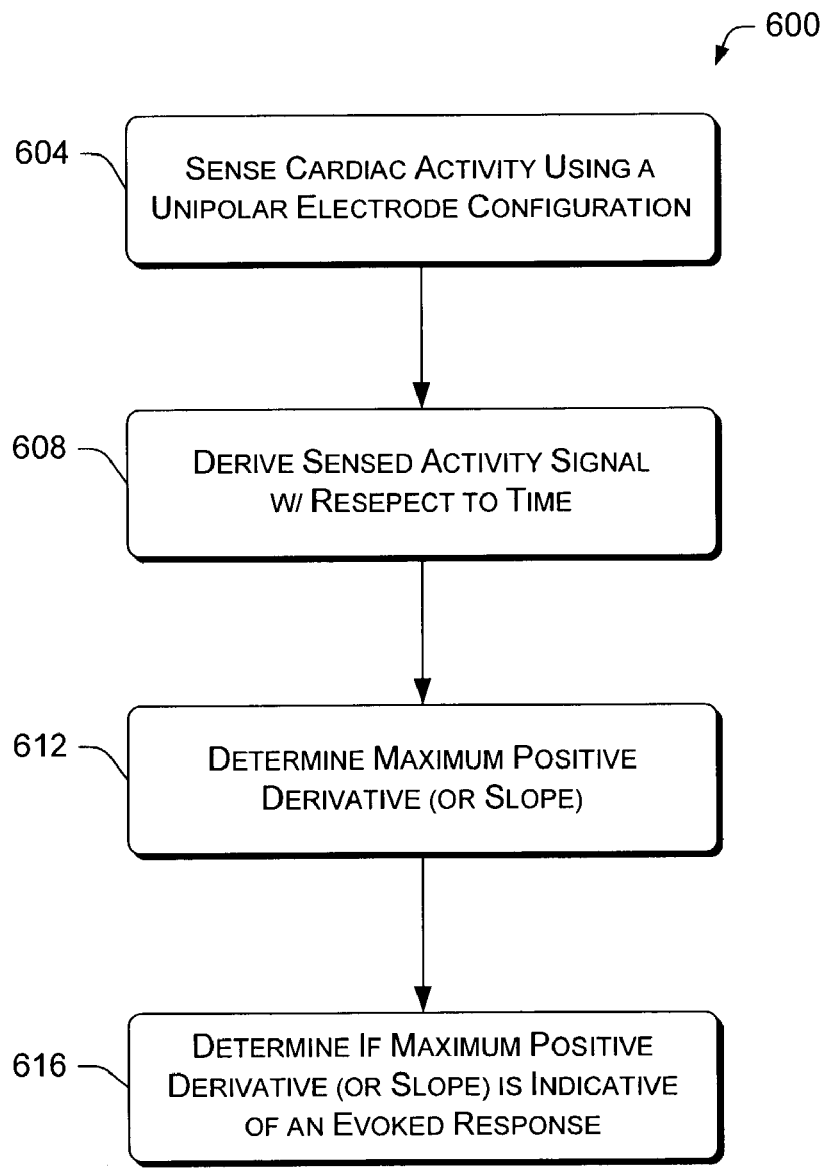
FIG. 14 is a block diagram of an exemplary method for detecting an atrial evoked response on the basis of a maximum positive derivative or slope.

An exemplary method for detecting an atrial evoked response 600 is shown in FIG. 14. In a sense block 604, an implantable pacing device (e.g., device 100 of FIGS. 1 and 2) senses cardiac activity using a unipolar electrode configuration (e.g., a ring and case configuration), typically after an atrial pacing pulse administered using a bipolar electrode configuration (or, alternatively, a unipolar configuration) and in the form of an electrical signal. In a derivation block 608, the implantable pacing device determines a derivative of the sensed activity signal with respect to time. Next, in a determination block 612, the implantable pacing device determines the maximum derivative of the sensed activity signal with respect to time for a time period commencing at or near an administered atrial pacing pulse or commencing approximately 25 milliseconds to 50 milliseconds after an administered bipolar atrial pacing pulse. In one example of the exemplary method 600, the time period commences at approximately 40 milliseconds after an administered bipolar atrial pacing pulse. In a second determination block 616, the implantable pacing device determines if the maximum positive derivative (or slope) is indicative of an atrial evoked response. The implantable pacing device optionally makes this determination by comparing the maximum positive derivative (or slope) to a parameter value. For example, if the maximum positive slope is 100 (arbitrary units of voltage over time) and the parameter value is 80 (arbitrary units of voltage over time), then the implantable pacing device determines that an atrial evoked response occurred. Following this determination, the implantable pacing device optionally terminates sensing and/or analysis of the unipolar atrial signal (e.g., sensed using a ring and case configuration) until delivery of a subsequent bipolar atrial pacing pulse (or, alternatively, a unipolar atrial pacing pulse).

Figure 15:
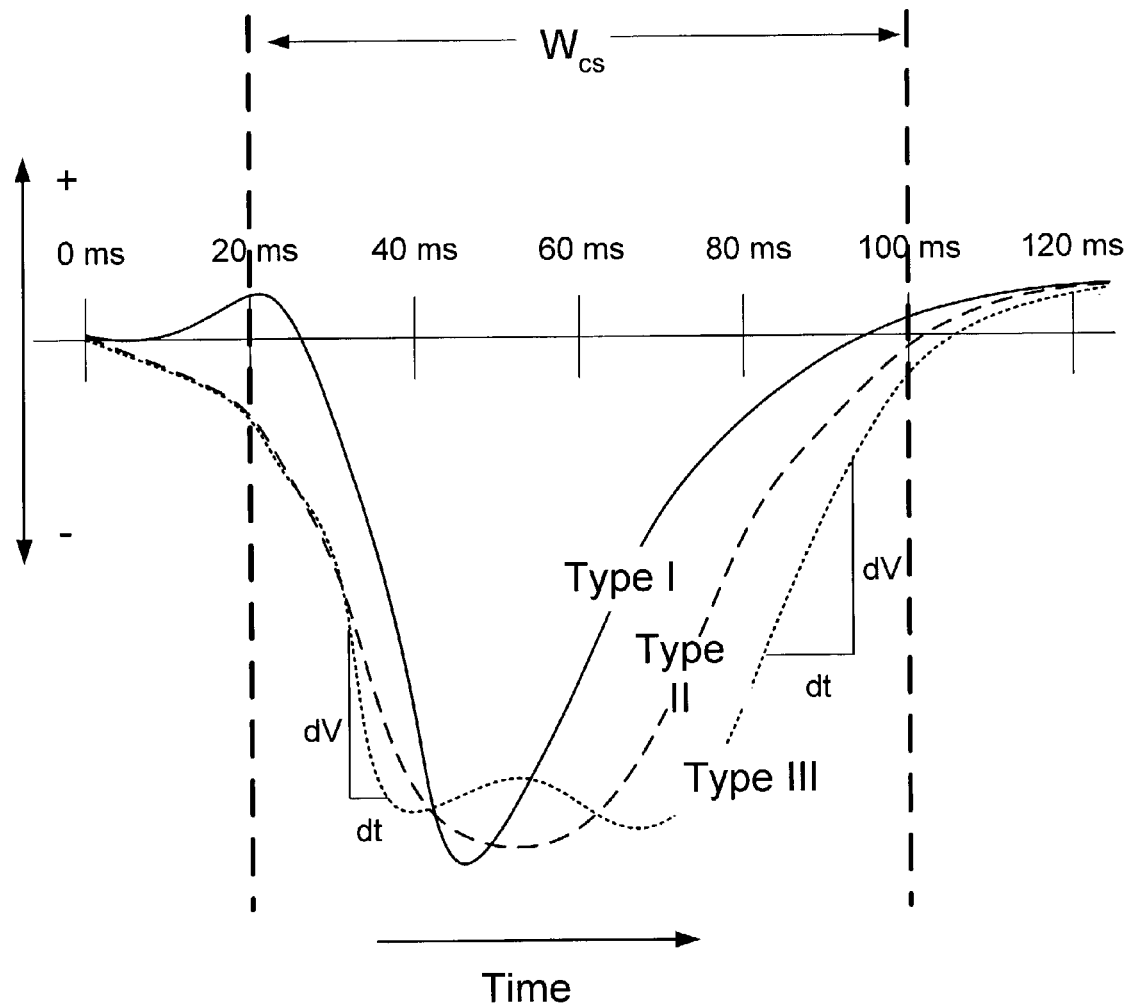
FIG. 15 is a diagrammatic plot, as shown in FIG. 10, further including a combined negative and positive slope window.

Referring to FIG. 15, an exemplary combined negative and positive slope time window ($W_{cs}$) is shown superimposed on the plot of FIG. 10. The combined slope time window ($W_{cs}$) begins at approximately 20 milliseconds and ends at approximately 100 milliseconds. Of course, the window may optionally commence at an early time and/or upon occurrence of an event and terminate at a different set time and/or upon occurrence of an event. At post-pulse times of approximately 30 milliseconds and approximately 90 milliseconds, the Type III generalized atrial evoked response shows time intervals (dt) and voltage intervals (dV) representative of derivatives of the Type III evoked response. In particular, the two derivatives correspond to a maximum negative derivative (or slope) and a maximum positive derivative (or slope) for the Type III response. Also note that the Type I and Type II responses also exhibit a maximum negative derivative (or slope) and a maximum positive derivative (or slope) within the same window ($W_{cs}$).

An exemplary method for detecting an atrial evoked response corresponding to a combined slope sensing window, as described with reference to FIG. 15, optionally includes various operational blocks of exemplary methods 500 and 600 shown in FIGS. 12 and 14. According to this exemplary method, determination of a maximum negative derivative (or slope) followed by determination of a maximum positive derivative (or slope) may enhance detection of atrial evoked responses. Further, in this exemplary method, and/or in other exemplary methods using derivatives (or slopes), comparison of derivative (or slope) to a threshold or parameter value may alleviate the need to determine a maximum (or maxima) and/or a minimum (or minima). In addition, derivatives (or slopes) may be time averaged and/or instantaneous.

Figure 16:
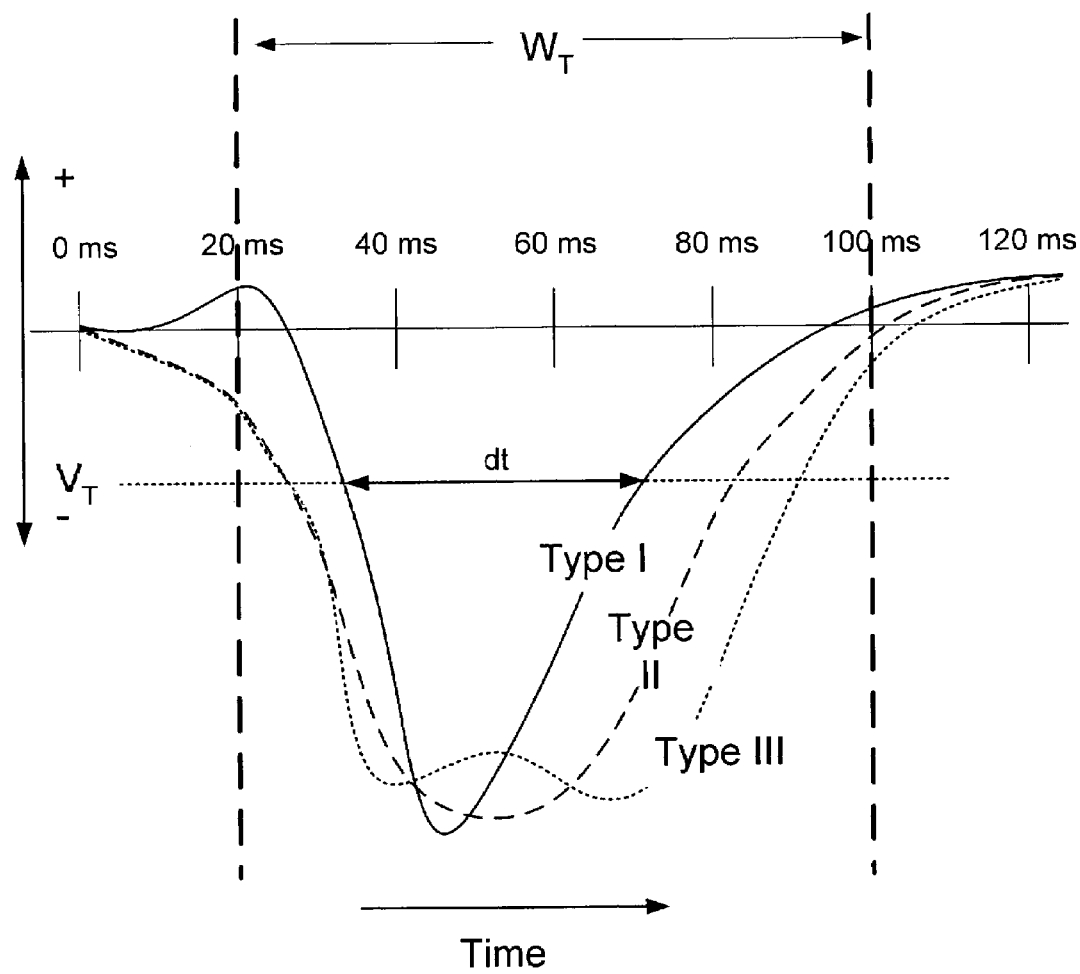
FIG. 16 is a diagrammatic plot, as shown in FIG. 10, further including a threshold voltage and a threshold voltage window.

Referring to FIG. 16, an exemplary voltage threshold ($V_T$) and exemplary voltage threshold time window ($W_T$) is shown superimposed on the plot of FIG. 10. The Type I, Type II and Type III atrial evoked responses cross the threshold between 20 milliseconds and 40 milliseconds and again between 60 milliseconds and 100 milliseconds. The label "dt" indicates the time between crossings for the Type I evoked response. Similar time intervals exist for the Type II and Type III responses.

Figure 17:
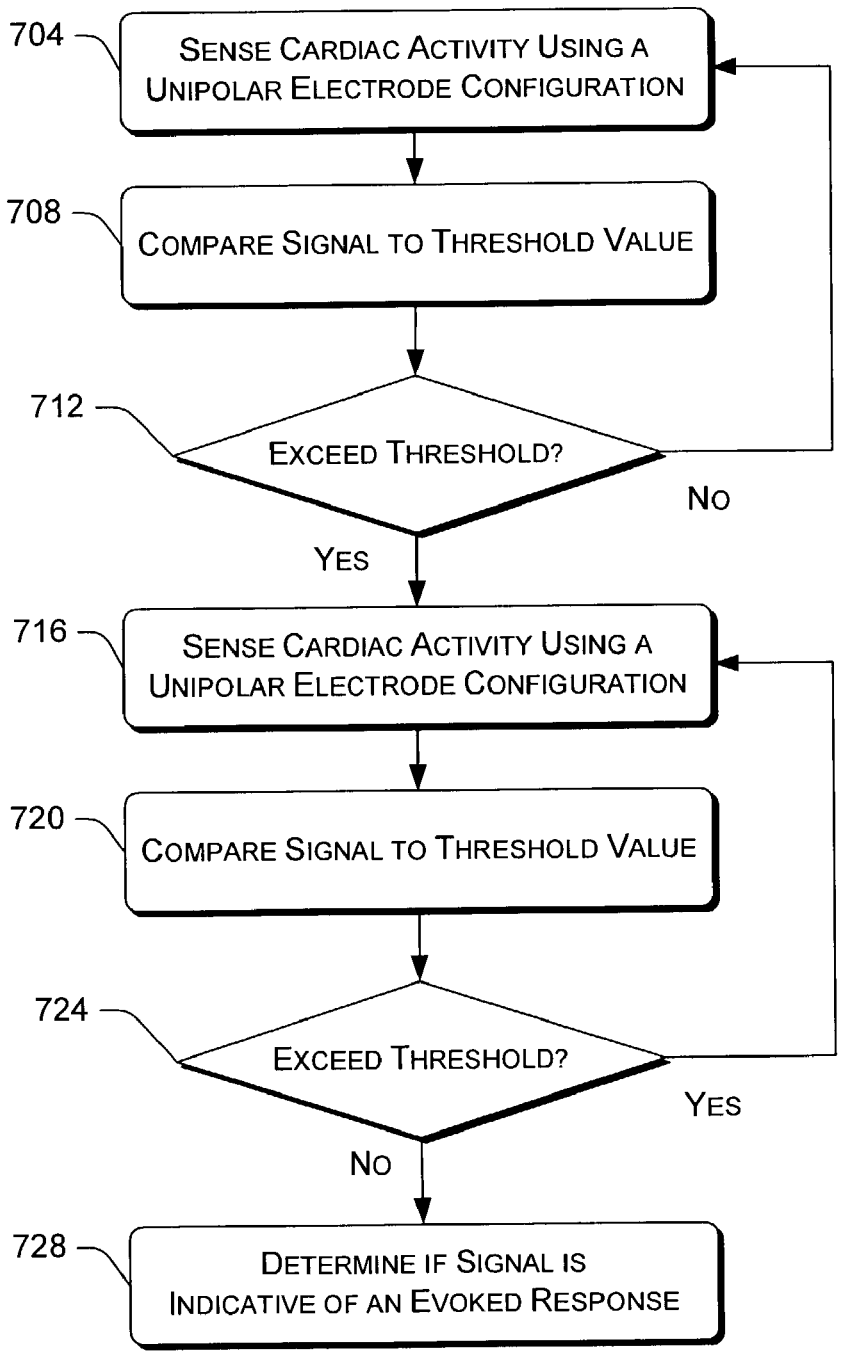
FIG. 17 is a block diagram of an exemplary method for detecting an atrial evoked response on the basis of a threshold value and/or a time interval.

Referring to FIG. 17, an exemplary method 700 for detecting an atrial evoked response is shown. In a sense block 704, an implantable pacing device (e.g., device 100 of FIGS. 1 and 2) senses cardiac activity using a unipolar electrode configuration (e.g., a ring and case configuration), typically after an atrial pacing pulse administered using a bipolar electrode configuration (or, alternatively, a unipolar configuration) and in the form of an electrical signal. In a comparison block 708, the implantable pacing device compares the signal to a threshold value. Next, in a check block 712, the implantable pacing device determines if the signal exceeded the threshold value. If the signal did not exceed the threshold value, then the method returns to the sense block 704; however, if the signal exceeds the threshold value, then sensing continues in another sense block 716. Another comparison block 720 and another check block 724 follow the second sense block 716. In the second check block 724, if the signal exceeds the threshold value, then sensing continues via the second sense block 716; however, if the signal does not exceed the threshold value, then a determination block 728 determines whether the signal is indicative of an atrial evoked response. For example, the determination block 728 optionally compares the time interval between the time at which the signal first exceeded the threshold value and the time at which the signal fell below the threshold value (e.g., the time interval "dt" as shown in FIG. 16). Of course, the determination block 728 may implement a different technique or a variety of techniques in making this determination. For example, the implantable pacing device may determine an integral value for the atrial evoked response signal over the time interval "dt" and/or over another interval. Other time intervals optionally commence at times greater than approximately 30 milliseconds, especially where electrode polarization and/or other artifacts associated with an atrial and/or other pacing pulse are a concern. Time intervals for integration and/or other signal analysis may end at times of up to and even exceeding approximately 120 milliseconds.

Exemplary methods may also use higher order derivatives and/or other mathematical techniques to analyze a sensed signal. For example, a second order derivative of a signal with respect to time can indicate existence of an inflection point, wherein a change in the sign of a first order derivative occurs. Inflection points appear in FIGS. 5 through 9, especially near a time of approximately 40 milliseconds. Exemplary methods may also rely on the difference between an atrial evoked response and a non-response because the non-response results in a relatively constant, DC-like voltage (see FIGS. 5 through 9). Integral, amplitude and/or other techniques are suitable for use in exemplary methods to distinguish between response and non-response signals shown in FIGS. 5 through 9 and thereby detect the presence of an atrial evoked response.

According to various exemplary methods described herein and/or equivalents thereof, an implantable pacing device delivers an atrial pacing pulse using a bipolar or a unipolar electrode configuration and senses cardiac activity using a unipolar electrode configuration, for example, but not limited to, a ring and case configuration. Based on the sensed cardiac activity, the implantable pacing device further detects whether or not an atrial evoked response has occurred. Data collected from trials on five patients indicate that such exemplary methods provide for an atrial evoked response signal that is not significantly (if at all) impaired by electrode polarization artifacts. Further, the atrial evoked response signal, on an individual patient basis, is relatively independent of pulse voltage for voltage levels that cause an atrial evoked response. And, for pulses that do not cause an atrial evoked response, unipolar ring and case sensing in a relatively "late" detection window yields a relatively constant, DC-like voltage. In addition, the atrial evoked response exhibits characteristics that are patient independent. Overall, such exemplary methods can provide for a robust manner to detect atrial evoked responses.

CONCLUSION

Although the exemplary methods and/or devices have been described in language specific to structural features and/or methodological acts, it is to be understood that the subject matter defined in the appended claims is not necessarily limited to the specific features or acts described. Rather, the specific features and acts are disclosed as exemplary forms of implementing the claimed exemplary methods and/or devices.

What is claimed is:

1. A method for sensing cardiac activity in an atrium of a patient's heart, comprising:
   delivering a pulse to the atrium using an electrode configuration that includes at least a pulse cathode electrode;
   sensing cardiac activity in the atrium using a unipolar electrode configuration to provide a sensed signal with respect to time wherein the unipolar electrode configuration does not include the pulse cathode electrode;
   determining a maximum positive first derivative value of the sensed signal and a maximum negative first derivative value of the sensed signal;
   comparing the maximum positive first derivative to a positive first derivative parameter;
   comparing the maximum negative first derivative to a negative first derivative parameter; and
   determining the pulse caused an atrial evoked response when the maximum positive first derivative is greater than the positive first derivative parameter and the maximum negative first derivative is less than the negative first derivative parameter;
   wherein the positive first derivative parameter is different from the negative first derivative parameter.

2. The method of claim 1 wherein the sensing commences at least 15 milliseconds after the delivering.

3. The method of claim 1 wherein the determining of derivative values commences at least 15 milliseconds after the delivering.

4. A method for sensing cardiac activity in an atrium of a patient's heart, comprising:
   delivering a pulse to the atrium using a bipolar electrode configuration including at least a first tip electrode and a second electrode;
   sensing cardiac activity in the atrium using a unipolar electrode configuration comprising the second electrode to provide a sensed signal with respect to time;
   determining a maximum positive first derivative value of the sensed signal and a maximum negative first derivative of the sensed signal;
   comparing the maximum positive first derivative to a positive first derivative parameter;
   comparing the maximum negative first derivative to a negative first derivative parameter; and
   determining the pulse caused an atrial evoked response when the maximum positive first derivative is greater than the positive first derivative parameter and the maximum negative first derivative is less than the negative first derivative parameter;
   wherein the positive first derivative parameter is different from the negative first derivative parameter.

5. The method of claim 4 wherein the sensing commences at least 15 milliseconds after the delivering.

6. The method of claim 4 wherein the determining of derivative values commences at least 15 milliseconds after the delivering.

* * * * *